US006328811B1

(12) United States Patent
Martin et al.

(10) Patent No.: US 6,328,811 B1
(45) Date of Patent: *Dec. 11, 2001

(54) METHODS AND SYSTEMS FOR CLEANSING THE SKIN

(75) Inventors: John P. Martin, Pfafftown, NC (US); Susan M. Skewes, New London, CT (US)

(73) Assignee: Incline Technologies, Inc., Carson City, NV (US)

(*) Notice: Subject to any disclaimer, the term of this patent is extended or adjusted under 35 U.S.C. 154(b) by 0 days.

This patent is subject to a terminal disclaimer.

(21) Appl. No.: 08/933,901

(22) Filed: Sep. 19, 1997

Related U.S. Application Data (63) Continuation-in-part of application No. 08/542,964, filed on Oct. 13, 1995, now Pat. No. 5,702,992, which is a continuation-in-part of application No. 08/266,963, filed on Jun. 27, 1994, now abandoned, which is a continuation-in-part of application No. 08/203,230, filed on Feb. 28, 1994, now abandoned.

(51) Int. Cl.[7] ............................................ B08B 7/00
(52) U.S. Cl. ................................... 134/6; 134/19; 134/42
(58) Field of Search ................................ 134/6, 19, 42

(56) References Cited

U.S. PATENT DOCUMENTS

| 1,507,707 | 9/1924  | Morganstern. |
|-----------|---------|--------------|
| 1,619,180 | 3/1927  | Benussi. |
| 3,154,462 | 10/1964 | Smith, II .............................. 161/154 |
| 3,191,257 | 6/1965  | Smith, II .............................. 28/72.2 |
| 3,404,010 | 10/1968 | Wilds .................................... 99/131 |
| 3,483,601 | 12/1969 | Smith, II . |
| 3,608,708 | 9/1971  | Storandt ............................. 206/46 R |
| 3,638,789 | 2/1972  | Tuszewski ........................ 206/63.2 R |
| 3,965,519 | 6/1976  | Hermana ............................. 428/290 |
| 4,065,826 | 1/1978  | Hough .................................... 15/227 |
| 4,090,844 | 5/1978  | Rowland ................................. 8/120 |

(List continued on next page.)

FOREIGN PATENT DOCUMENTS

| 3331573 | 3/1985 | (DE) . |
|---------|--------|--------|
| 032793  | 7/1981 | (EP) . |
| 2647091 | 11/1990 | (FR) . |
| 2163947 | 3/1986 | (GB) . |
| 2190289 | 11/1987 | (GB) . |
| 2211093 | 6/1989 | (GB) . |
| 2218430 | 11/1989 | (GB) . |
| 63160658 | 4/1988 | (JP) . |

OTHER PUBLICATIONS

Foster, J., "Needle Felting Technology", Nonwoven Fabrics Forum, Hunter Chemistry Auditorium, Clemson University, Aug. 15–18, 1994, 20 pgs.

Vaughn, E. A., "What is a Nonwoven?", School of Textiles, Fiber and Polymer Science at Clemson University, Aug., 1994, 9 pgs.

(List continued on next page.)

Primary Examiner—Zeinab El-Arini
(74) Attorney, Agent, or Firm—Christie, Parker & Hale, LLP (57) ABSTRACT

A kit for bathing a patient or for personal bathing includes a sealed polyethylene bag containing a plurality of cloths impregnated with a cleansing solution. The cloths are a needle-punched blend of cotton and cellulose acetate for softness and low cost. Furthermore, an anti-microbial agent is carried by the cellulose acetate to prevent the growth of bacteria, yeast and fungus and the package carries another anti-microbial solution as a preservative. The cleansing solution is a non-ionic, non-rinsing mixture of surfactants, emollients or humectants, vitamin E and de-ionized water. The kit is heated and then each cloth is used on a different part of the body and disposed of after use to prevent cross contamination.

16 Claims, 5 Drawing Sheets

U.S. PATENT DOCUMENTS

| | | | |
|---|---|---|---|
| 4,091,491 | 5/1978 | Hoffman | 15/227 |
| 4,112,167 | 9/1978 | Dake et al. | 442/123 |
| 4,343,403 | 8/1982 | Daniels et al. | 206/812 |
| 4,347,931 | 9/1982 | Ginger et al. | 206/438 |
| 4,523,348 | 6/1985 | Petrie | 15/227 |
| 4,615,937 | 10/1986 | Bouchette | 442/123 |
| 4,725,489 | 2/1988 | Jones et al. | 442/123 |
| 4,749,080 | 6/1988 | Toohey | 206/210 |
| 4,781,974 | 11/1988 | Bouchette et al. | 428/288 |
| 4,788,733 | 12/1988 | Lerner | 15/104.94 |
| 4,810,567 | 3/1989 | Calcaterra et al. | 428/224 |
| 4,837,079 | 6/1989 | Quantrille et al. | 442/123 |
| 4,847,071 | 7/1989 | Bissett et al. | 424/59 |
| 4,877,816 | 10/1989 | Murabayashi et al. | 521/92 |
| 4,902,283 | 2/1990 | Rojko et al. | 604/290 |
| 4,948,585 | 8/1990 | Schlein | 424/404 |
| 4,959,881 | 10/1990 | Murray | 15/227 |
| 4,964,188 | 10/1990 | Olson | 15/227 |
| 5,019,058 | 5/1991 | Storandt | 604/290 |
| 5,050,737 | 9/1991 | Joslyn et al. | 206/494 |
| 5,229,105 | 7/1993 | Wilmsmann | 424/59 |
| 5,229,963 | 7/1993 | Wilmsmann | 424/59 |
| 5,256,417 | 10/1993 | Koltisko | 424/402 |
| 6,206,863 | 3/2001 | Skewes et al. | 604/290 |

OTHER PUBLICATIONS

Vaughn, E. A., "Principles of Woven, Knitted, and Nonwoven Fabric Formation", Nonwoven Fabrics Forum, School of Textiles, Fiber and Polymer Science, Hunter Chemistry Auditorium, Clemson University, Aug. 15–18, 1994, 30 pgs. Susan M Skewes, "The Bag Bath, a Theory Based Alternative to the Traditional Bed Bath", Aug. 1992.*

Susan Skewes, "No More Bed Baths", Jan. 1994, RN Magazine.*

* cited by examiner

METHODS AND SYSTEMS FOR CLEANSING THE SKIN

This is a continuation-in-part of application Ser. No. 08/542,964 filed Oct. 13, 1995, now U.S. Pat. No. 5,702,992, which itself is a continuation-in-part of application Ser. No. 08/266,963, filed Jun. 27, 1994, now abandoned, itself a continuation-in-part of application Ser. No. 08/203,230, filed Feb. 28, 1994, now abandoned.

FIELD OF THE INVENTION

The present invention relates generally to an improved non-woven fabric cloth and a method of making the fabric cloths for use in the system for cleansing the skin disclosed in the foregoing noted applications. More particularly, the present invention is preferably embodied in a kit including the fabric cloths impregnated with a solution for cleansing a patient in a hospital, a nursing home or for personal bathing.

BACKGROUND OF THE INVENTION

The skin is the largest organ of the human body. As a boundary layer, it has two functions: containing other organs of the body and acting as a barrier. Its effectiveness as a barrier depends on its physical integrity. Preserving that integrity is an important part of maintaining good health. However, when skin is dry, it tends to itch, flake and crack; skin dryness leads to a higher incidence of psoriasis and hastens the formation of pressure ulcers, a concern for all patients but an especial concern to elderly and orthopedic patients. In the United States, pressure ulcers cost between $10 billion and $15 billion to treat each year, an average of $45,000 each. The in-hospital death rate for patients with pressure ulcers has been estimated to be as high as 23%. Accordingly, the United States Department of Health and Human Services, Public Health Service, Agency for Health Care Policy & Research, published guidelines in 1992 consistent with the recommendations of the National Pressure Ulcer Advisory Panel that are directed to care of patients in hospitals (Clinical Practice Guideline No. 3, Pressure Ulcers in Adults: Prediction and Prevention). The guidelines specify avoiding hot water, low humidity, irritating and drying of the skin and encourage the use of mild cleansers in bathing patients.

Dryness of skin can result from a number of factors, including aging, exposure to wind, heat, air conditioning, and washing with soap. Because the skin of the elderly has less subcutaneous fat, the aging process has been associated with a decrease in the ability of the lipids in skin to bind water. It has been estimated that 59% to 75% of the elderly have some degree of skin impairment upon admission to hospitals.

Washing with soap is a particular concern for skin condition and health in hospitals. The traditional bath given to patients involves the use of wash cloths, soap and a plastic basin. The basin is filled with warm water and taken to the patient's bedside. The patient is bathed by applying soap to a cloth, rubbing the cloth over the patient's skin, and rinsing the skin with water. The patient's skin is then dried using a towel. The textbook approach recommends frequent changes of the water and the wash cloths.

In practice, because of time constraints, the textbook approach is seldom observed. Use of the same water and cloth for bathing the entire body results in areas of the patient's body becoming contaminated by bacterial flora carried from other parts. Bars of soap and basins (often stored with bedpans in a warm, dark cabinet between use with the same or a different patient) encourage culture gram-negative bacteria which are pathogenic and can cause impairment and infection of skin tissues. Studies have shown that a patient is usually microbiologically more contaminated after the bath than before.

Another problem with the traditional bathing approach is friction against the skin. Friction from the use of wash cloths and towels damages skin tissue. Furthermore, to reduce the cost of linens, a major cost factor in hospital budgets, towels and wash cloths of inferior quality are purchased for patient bathing and they are used longer before being discarded. Consequently, the texture of towels and wash cloths for bathing patients is coarser, further exacerbating the condition of their skin.

Furthermore, the traditional bathing procedure is still time consuming, requiring 30–45 minutes per patient per day, and has a relatively high direct cost because of the time involved.

Washing with soap also has a high indirect cost. There is a protective coating on the skin formed from sebum secreted by the hair follicles and dead skin cells. This coating, or "acid mantle," has bacteriostatic and fungistatic properties. Soap impairs the skin in two ways. First, soap emulsifies skin lipids which hold moisture, leaving the skin drier; and, second, soap, being alkaline, destroys the acid mantel of the skin. Washing with soap is therefore a major physiological risk to the individual, because bacteria can survive longer on the soap-washed skin and can gain entrance to the interior skin layers and the blood stream through dried, cracked skin or pressure ulcers.

In the January 1994 issue of RN Magazine, a procedure was reported for bathing patients that is not based on this traditional procedure. The new procedure involves use of a set of wash cloths soaked in a dilute solution of a cleanser composed substantially of mild soap and water. This cleanser does not need to be rinsed; it evaporates quickly from the skin. The cloths are placed in a plastic bag, heated in a microwave oven until warm, and then applied to defined areas of a patient's body, one cloth per area. The cloths are laundered between uses. There is no basin. The cleanser is not rinsed, but dries quickly without toweling. Only the areas with large skin folds are gently patted dry. An extensive study of this procedure compared to the traditional one showed that the patients felt cleaner, skin condition was better and the costs were reduced by a factor of four, largely because of less time being needed to bathe a patient. Skin integrity improved statistically by 56% from admission to discharge from the hospital. However, the time taken to bathe a patient was partially offset by the labor involved in preparing the cloths. Furthermore, the cloths cannot be prepared far in advance because of the limited storage space and, more importantly, the inevitable growth of bacteria associated with this procedure.

There have been other attempts to develop a product for bathing a patient or cleansing skin. For example, Storandt (U.S. Pat. No. 5,019,058) teaches an applicator mitt for a variety of uses including applying ointment for treating injured parts of the body. Storandt's mitt is in the form of a pouch within a heat sealed package. The material is two-ply, including a non-woven fabric and a thermoplastic film such as polyethylene or EVA.

Two mittens have been developed for use in changing the diapers of babies and in performing the associated cleansing. The more recent of these is by Rojko, et al. (U.S. Pat. No. 4,902,283) and is a simple cylindrical mitt for cleaning babies, with an outer layer of cotton and a water-repellent inner layer. The cotton layer is stitched and the inner layer can be made of polypropylene. Rojko, et al. also teach the rotation of the mitt by 180° to use "the other side."

The other baby mitten is disclosed by Lemer in U.S. Pat. No. 4,788,733. He teaches a two-ply glove for cleaning babies. Lemer also teaches impregnating his mitten with a cleaning solution.

In U.S. Pat. No. 4,523,348, Petrie describes a so-called nurse's mitt expressly for bathing a patient. This mitt is broadcloth-backed terry cloth and has features designed for convenience in gripping the mitt.

Ginger, et al. (U.S. Pat. No. 4,347,931) also provide a mitt for cleaning a patient as well as applying an antiseptic. Their mitt is rectangular and two-ply, with a plastic, non-porous inner layer and an absorbent outer layer. The mitt, which is described as disposable, is impregnated with a cleaning solution and placed in an outer package that is opened just prior to use.

Many presently-available fabrics towels and wash cloths are coarse in texture and irritating to the skin; softer fabrics are low in tensile strength and tend to disintegrate when wet. There remains a need for a system for bathing that is effective for skin cleansing, practical, inexpensive and minimizes damage to the protective acid mantle of the skin.

SUMMARY OF THE INVENTION

According to its major aspects and broadly stated, the present invention provides a soft, inexpensive cloth carrying an anti-microbial agent in its fibers and impregnated with a non-ionic cleanser for cleansing the skin. The cleanser may include an anti-microbial agent such as polyhexamethylene biguinide at a 1% by weight concentration. In one embodiment, there are a set of cloths sufficient for a whole body bath, placed in a sealed polyethylene bag suitable for heating by microwaves. The cleanser, which requires no rinsing, dries quickly, does not damage the skin's acid mantle and leaves a protective emollient, is preferably a mixture that includes at least one non-ionic surfactant, vitamin E, a humectant and/or an emollient and de-ionized water. The cloth is a soft, inexpensive, non-woven, needle-punched selected cotton fiber or a blend of fibers selected so as to avoid abrading the skin and that can be used once and then discarded. The anti-microbial agent in fibers of the cloth inhibits microbial growth so that the cloths can be prepared and stored well in advance of use.

The cloth, in one form, may be made by treating high quality cotton fibers or by blending cotton, polyester or other synthetic fiber and cellulose acetate fibers. The fibers, of cotton only or a blend, may be randomly oriented in a carding machine which produces a web of fibers, blended or uniform, in a layer that may them be formed into two or more layers by cross-lapping. The layer or layers if cross-lapped and formed into a batt is then needle punched to form an entangled web which is subsequently cut to form the cloth elements. Alternately, layers may be formed and the batt may be formed with a first layer and a second layer, although this format is somewhat more expensive. The fibers of the second layer are oriented at approximately a right angle with respect to the fibers of the first layer. The layers are then cross-lapped and entangled by needle punching to form the cloth. Next, the cloth is cut into squares, soaked in the cleanser and then the excess portion of cleanser is wrung out, leaving them moistened rather than wet. The soaking and cutting of the batt may be done at several different stages of the manufacturing process and the foregoing is one example. The cloths are packaged and the packages sealed until use. Just prior to use, the packages can be heated for the comfort of the user.

For some uses, the cotton will be sterilized or may carry an anti-microbial agent as described herein and may have a number uses not requiring sterilization including a bath package as well as a batting for quilt sewing and dry wiper uses.

Use of the present invention should significantly lessen the incidence of pressure ulcers. Perhaps more importantly, its use is believed to be essential in certain types of cases of especially high risk for infection, such as bone marrow transplant victims, burn victims, and other cases where the auto-immune system of an individual is suppressed, such as AIDS patients.

An important feature of the present invention is the combination of a plurality of cleanser-impregnated cloths and the container. The exact number depends on use, as will be described in more detail in the Detailed Description. This combination of cloths and container provides a single-use, yet complete, sterile, compact personal bathing kit that can be made to high quality standards well in advance of need. The kit may be heated slightly for comfort, and the cloths can then be used to cleanse a number of zones such as eight zones of a human body. Each cloth can clean one zone of the body. One kit bathes one patient, and each kit is discarded after use. Thus, the kits lend themselves to a manufacturing process that will minimize the labor involved in kit assembly and assures kit cleanliness, sterility, uniformity, and accurate formulation of the cleansing mixture. The system of the present invention complies with the National Pressure Ulcer Advisory Panel recommendations, avoids cross contamination of the patient and is likely to reduce the incidence of nosocomial infections. Furthermore, the manufacturing of a single use "kit" assures that the quality of the kit is uniformly high and that the kits are compact to minimize space storage requirements.

The non-woven cotton or blend of cotton, cellulose acetate and polyester for the material of the cloths is another feature of the present invention. The cloths are durable and can remove dirt, yet are soft, and do not chemically react with either the impregnated solution or the patient's body. The non-woven cloths are chemically stable to microwaves and are heat retentive. Moreover, the cloths, which can be manufactured in any convenient shape, are absorbent, assuring the retention of enough solution for effective cleansing, and soft and smooth for low friction. Finally, these cloths are simple and inexpensive to manufacture, making them more affordable as a disposable item than traditional, woven cotton wash cloths and more effective than paper products. In a preferred form, the cotton fibers, after bleaching and scouring, are coated with a silicone finish which further reduces frictional abrasion and improves the migration of the anti-microbial agent in the cloth to enhance the effectiveness of the agent. In one form, the cotton fibers comprise from 50% to 75% by weight of the cloth, the anti-microbial impregnated fibers such as cellulose acetate comprise 21% to 25% by weight. A synthetic fiber such as polyester, acrylic or nylon will comprise from 0 to 25% by weight of the cloth.

Another important feature of the present invention is the cleanser itself. By being substantially non-ionic, as a result of the use of non-ionic surfactants and de-ionized water, it cleanses without disturbing the acid mantle of the skin or leaving behind minerals and chlorine. Damage to the skin layer and its bacteriostatic and fungistatic properties is thereby avoided. Preservation of the acid mantle is especially important in a hospital environment where bacteria abound and the patient's resistance to nosocomial infection may be less than that of a healthy individual. De-ionized water does not have ions present in the same concentrations that are present in tap water. The additional ingredients are believed to soften, soothe, nourish and protect the skin.

Still another feature of the present invention is the method of impregnating the cloths during the manufacturing process. The cloths are first saturated with cleansing solution, then the excess is removed by squeezing them with sufficient pressure so that just the excess is removed. This method assures the even distribution of the solution in just sufficient quantity for the task of cleansing. Removing excess solution also reduces weight and bulk of the kit, making it easier and less expensive to transport and store large numbers of kits.

Being able to sterilize the kit at a manufacturing facility is another feature of the present invention. Sterilization can be achieved by subjecting the kit to ultraviolet light, electron beam, or gamma radiation or, preferably, by adding an anti-microbial agent to the product. Sterilization extends the shelf life indefinitely and allows use of the kits following emergencies, natural disasters, military action, and hospital emergencies involving loss of water. The present invention can also be used in locations where clean water is not readily available, such as by those who live in remote areas, by campers, and by those on boats. In the cloth of the invention, in the event of damage to the package, anti-microbial action will be maintained by the use of the anti-microbial agent in the acetate fibers.

The sealable, moisture-proof, microwave-transparent container is another feature of the present invention because it enables the cloths to be impregnated in advance without concern that they might dry out or lose effectiveness, either during storage or during warming. Additionally, the container itself is sterilizable using a number of sterilization techniques and does not react or degrade upon contact with the cloths or the impregnated solution. The choice of fibers for the blend is a major feature of the present invention. Cotton is selected for softness; polyester fibers for strength, less cost and, as long as they are fine fibers—less than three denier—they are also soft. The percentage of cellulose acetate in the blend provides sufficient carrier for the anti-microbial agent but not enough to significantly affect cost or softness as this fiber is similar to cotton in softness and absorbency.

The inclusion of the anti-microbial agent such as chlorinated phenoxy compound in the preferred embodiment is another major aspect of the present invention. The agent prevents the culturing of microbial agents during the shelf life of the product and, because it can be carried by one of the components of the fiber blend, is easily and naturally incorporated into the cloth. Moreover, the incorporation of such agents at the appropriate concentrations in some of the fibers will assure activity of the agent or agents after disposal so that the cloths is self sanitizing. This will enhance the safety of the disposed of cloths in hospital or other environments. The use of an anti-microbial agent also is likely to minimize the need for adding preservatives to the cleansing solution when present in the cleansing solution at the level of about 5,000 ppm although higher levels may eliminate the need for any preservative. Further, the anti-microbials used have low toxicity and thereby facilitate disposal.

The use of needle felting, sometimes called needle punching, to entangle the fibers of the fiber blend is another important feature of the present invention. Needle punching not only reduces cost from that of a woven cloth but also produces a softer cloth, especially in the case where no warp thread or other type of support carriers typically used in needle punching is used, as is the case here. The non woven entanglement process may be carried out on a wet or dry web.

Other features and advantages of the present invention will be apparent to those skilled in the art from a careful reading of the Detailed Description presented below and accompanied by the drawings.

DETAILED DESCRIPTION OF THE INVENTION

The present invention is a package of articles for cleansing the skin with the package having an anti-microbial system. The article in its simplest embodiment is a soft cloth impregnated with a non-ionic cleansing solution and carrying in at least some of the fibers of the cloth an antimicrobial agent to prevent bacterial, fungal and yeast growth on the cloth and the package having usually in liquid form a preservative which is within the range of 0.5 up to 2% by weight and preferably is 1% by weight of polyhexamethylene biguinide (PHMB). Preferably, the present invention is embodied as a kit containing a set of these cloths in a sealed polyethylene bag. The bag and cloths are suitable for heating in a microwave oven to warm the cloths just prior to use. In this form, the kit is all that is needed for bathing a patient or oneself. The cleanser is formulated to clean without rinsing or towel drying, without disturbing the acid mantle of the skin, and to leave a protective emollient to protect the skin.

The number of cloths in a kit depends on the use and may vary widely. In its primary configuration, there are, as an example, eight cloths for the eight zones of the body. A smaller kit, containing four cloths, is useful for partial bathing or episodes of incontinence. A still smaller kit of two cloths is preferred for small children and cleansing just the face and hands. Finally, for bathing an incontinent patient, a set of ten cloths is preferred. In one embodiment, the package may contain in solid or liquid form the same anti-microbial agent that is incorporated in some of the fibers and this will be effective at a concentration of 1,500 ppm of the total weight of the cloths.

The cloths are preferably designed to be disposable; that is, they are made of cost-effective and biodegradable or recyclable materials and are mass produceable so that the cost of the kit is lower than the cost of laundered wash cloths. Therefore, in the present context, disposable means that the cloths are used once and then thrown away in an appropriate receptacle for disposal or recycling, but not laundered for reuse. In this form, a non-biodegradable fiber would be avoided.

In order to provide a soft, inexpensive cloth, the cloth is made from non-woven fibers such a cotton or a blend of fibers. Specifically, the blend of fibers for the cloth is composed of cotton and cellulose acetate fibers. The cotton fibers provide softness and good heat retention so that the cloths do not cool too rapidly after heating. Heat retention is especially important when the cloths are in the kit because there may be eight or more, all of which are heated at one time and then used one at a time. If the cloths cool too rapidly, those used last will be less comfortable for the patient or bather than those used first. If bathing a patient, reheating may not be practical.

The use of polyester fibers will provide strength where needed and, as a filler reduces cloth cost. Furthermore, as long as the polyester fibers are of small diameter, preferably less than three denier, they can still be soft. The biodegradablility, however, will be reduced.

Cellulose acetate fibers serve to carry the anti-microbial agent, about which agent additional detail follows. As long as the percent of cellulose acetate fibers is less than about 25% by weight, cost and softness are not compromised. In the p referred embodiment of the cloth of the present invention, the cellulose acetate fibers are not less than approximately twenty percent, the cotton not more than 60% and the polyester not more than 25% of the total fibers by weight. In another formulation, the cellulose acetate fibers may constitute 40% by weight of the total fibers which will raise the anti-microbial concentration resulting from the increase presence in the acetate to about 8000 ppm. In such a form, the need for any other anti-microbial agent may be eliminated.

Figure 1:
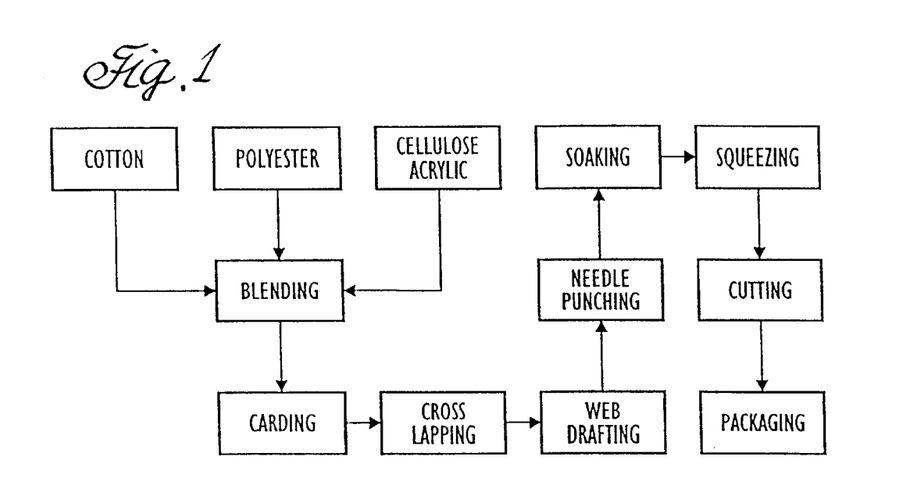
FIG. 1 is a schematic view of the process of making the cloth according to a preferred embodiment of the present invention.

To briefly review the process and referring to FIG. 1, the cotton, polyester and cellulose acetate fibers are individually weighed into hoppers and then combined and blended where different fibers are being used. A Lintmaster machine sold by Hergerth Hollingsworth Gmbh is preferably used to clean and open the cotton fibers to improve the quality of the finished product. The blended fibers are carded and a randomizer is used to create a uniformly dispersed, isotropic fiber oriented, carded web. The carded web is then passed to a cross-lapping machine 50.

Figure 2:
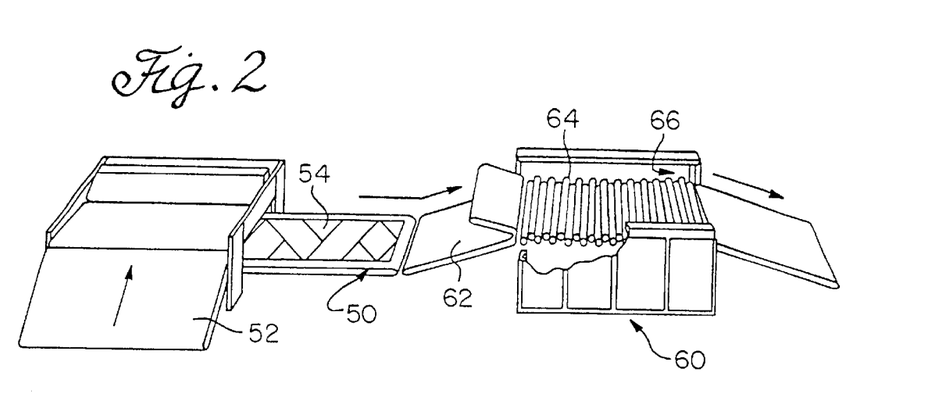
FIG. 2 is a perspective view of the cross-lapping and web drafting operations according to another preferred embodiment of the present invention.
Figure 4:
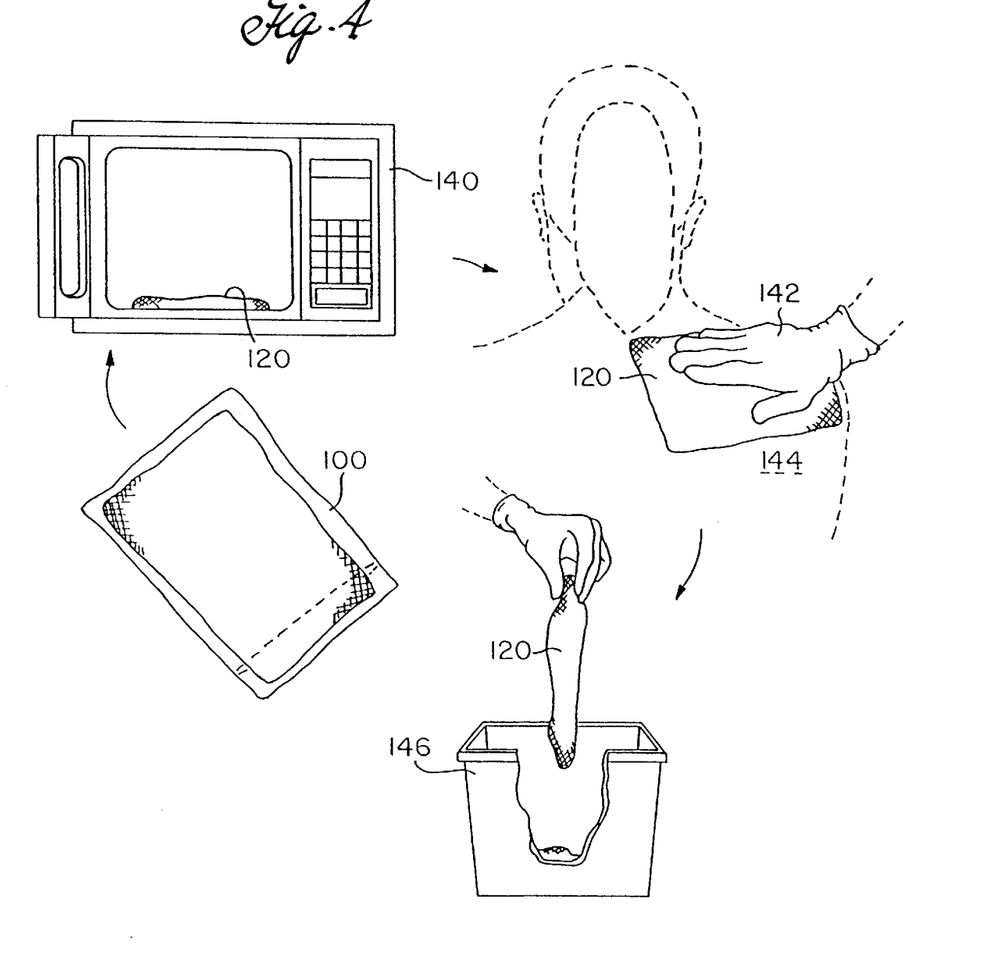
FIG. 4 is a schematic illustration of a kit and its use according to a preferred embodiment of the present invention.

A first conveyor 52 moves the material to t he cross-lapping machine 50. Cross-lapping machine 50 has a second conveyor 54 that is oriented at right angles to first conveyor 52, as indicated by arrows in FIG. 4. Conveyor 52 on cross-lapping machine 50 moves back and forth over conveyor 54 to deposit multiple pairs of the batt as it moves. The movement of first conveyor 52 is timed to be at a rate sufficient to form at least four and preferably six pair of layers to increase the thickness of the batt.

The multi-layer batt then may pass through a web drafter 60 that influences the orientation of the laid-down fibers to increase longitudinal strength of the web issuing therefrom and increases production of the draft. The cross-lapped batt enters the pivoting feed table 62 and moves through a plurality of rollers 64 of a pressing table 66 until coming out as a web.

Figure 3:
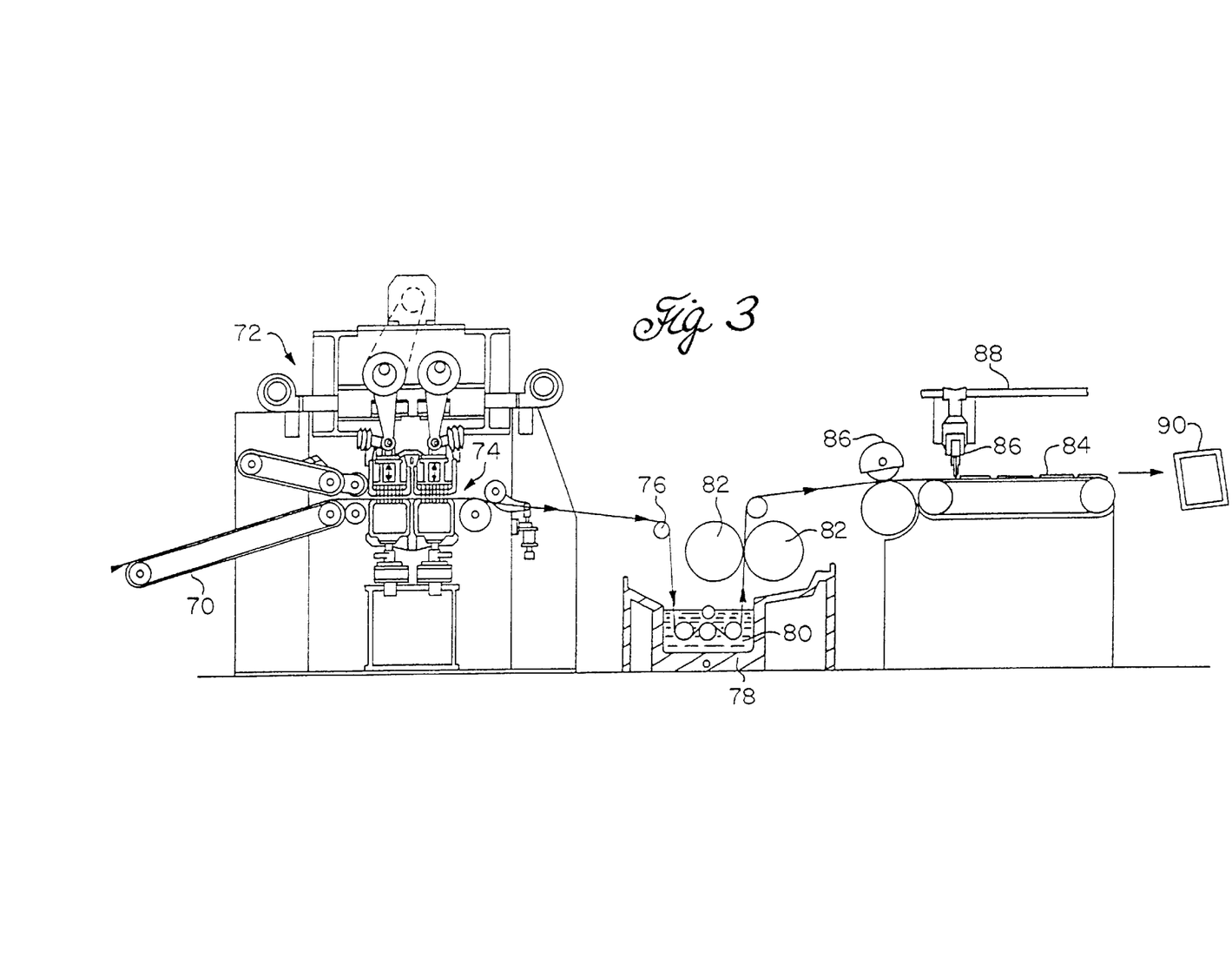
FIG. 3 is a side, partial cross sectional view of the needle punching, cloth impregnating and cutting operations according to a preferred embodiment of the present invention.

An example of a useful manufacturing process is shown in FIG. 3. The web is conveyed by a conveyor to a need punching machine 72 where a multiplicity of needles 74, preferably barbed, are punched through the web as it moves forward in the direction shown by the arrows to form the cloth. Needle punching, preferably at a high rate, such as over 1000 strokes per minute and most preferably about 2000 strokes per minutes, entangles the fibers of the various layers. The cloth is then conveyed by rollers 76 to a bath 78 of the cleansing solution at 80, where it is immersed to soak it, following which it is passed through rollers 82 to squeeze excess solution from the cloth. The cloth may be cut into appropriately sized squares or other shapes 84 by cutters 86 at cutting machine 88 and then a set of cloths placed in packages 90.

Soaking and then squeezing to impregnate the cloth with cleansing solution is necessary to ensure a just-sufficient amount of cleanser for effective cleaning without abrasion but no excess runs from the cloth when applied to the skin. Excess solution is wasteful, can run when the patient is bathed and affects evaporation time. Furthermore, removal of excess solution reduces both bulk and weight of the packaged kits. By careful packing of moistened cloths in a container, a ten-to-one reduction of bulk can be achieved over the former process using soaked wash clothes. Transportation and storage costs are reduced, as is the cost of the solution. These costs are not trivial, but are important, given the number of baths given patients in hospitals, to keep the cost associated with each disposable kit low.

There are a number of polymer-carried, anti-microbial agents available, and in particular there are anti-microbial plastics that release a single broad spectrum anti-microbial agent or multiple, targeted anti-microbial agents over time to continuously inhibit the growth of bacteria, fungi and yeast. One of these include chlorinated phenoxy compounds, such as that sold under the mark MICROBAN by Microban Products Company, which is preferred for the present invention. When incorporated into fibers such as the cellulose acetate, these compounds may significantly reduce or even avoid the need for preservatives in prolonging shelf life of the present cloth.

Typically, these polymers carry sub-micron chemicals in interstices of their molecular structure. Although these chemicals do not affect the physical properties of the polymer, they do interfere with the metabolism of microorganisms with which they come into contact. Many such anti-microbial agents are approved by the U. S. Environmental Agency as safe for human use.

Instead of the anti-microbial agent or in addition thereto, the contents of the kit may be sterilized by subjecting the cloths and container to ultraviolet light, electron beam, gamma radiation or other technique. These have the advantage of quick killing of any microbes in the fibers.

The cleanser is substantially non-ionic and very slightly acidic (pH $6.0+_{13} 0.5$) to preserve the acid mantle. An ionic cleanser, especially a strong base like soap, is harmful to this natural barrier. Preferably, the cleanser includes one or more surfactants (F68 and F108, for example), wetting agents that are non-ionic and that are dissolved in de-ionized water. De-ionized water will have fewer ions (and bacteria) than tap water and will also have a very slightly acidic pH between approximately 6.0 and approximately 6.5. The water alternatively can be purified through reverse osmosis, hyperfiltration or other technique. Also, the cleanser includes a hydrating factor or humectant, commonly called a moisturizer, for retaining water, or an emollient for holding the moisture, or both. Finally, the cleanser includes vitamin E and may also include a di-acid base such as polyhexamethylene biguanide as a preservative. Such a cleanser is manufactured by Sage Pharmaceutical and sold under the trademark DERMACLIN.

The manufacturer has alternatives in formulating the anti-microbial system. In one form, the fibers of the package may include about 20% by weight anti-microbial agent impregnated in the cellulose acetate fibers combined with sterilization of the formed package by gamma or electron beam radiation.

By reducing surface tension, surfactants enable the ingredients of the present solution to mix better with each other and they wet the skin surface better to enable the solution to spread more easily. Unlike cleansers, the preferred surfactant F68, regardless of concentration, does not inhibit the skin's ability to fight infection.

Vitamin E has been known to promote the healing of skin for several years. Humectants absorb water molecules; emollients hold moisture to the skin.

This cleansing mixture does not dry the skin, and it does not have to be rinsed. All of the ingredients remaining after evaporation are intended to remain on the skin to seal in moisture, yet without leaving a harmful or uncomfortable residue, hence the term "non-rinsing," which minimizes cross contamination and water exposure; specifically, the term "non-rinsing" is used to mean that the solution should not be rinsed from the body (although it can be), but is intentionally and preferably left to dry on the skin. While not wishing to be bound by theory, it is believed that the combination in the cleansing solution not only cleanses but protects, soothes, softens and nourishes the skin.

In one procedure, container 100 may be unsealed by tearing from a notched edge or along a perforated end, placed in a microwave oven 140 and heated until warm to the touch, but not hotter than 120° F. or 56° C. (see FIG. 4) and preferably about body temperature. Under controlled heating conditions, unsealing may be avoided prior to heating. Then container 100 is opened and one cloth 120 removed at a time. The user 142 washes a portion of the body of a patient 144. When that portion has been washed, cloth 120 is discarded into an appropriate waste receptacle 146, and the next cloth withdrawn from container 100. Each cloth is used in sequence and then discarded. This approach prevents the contamination of one part of the body by bacterial flora from another.

The present invention is ideally suited to almost any carrier member that can be applied to the skin. However, its uses are not limited to humans and in some circumstances, the washing of animals may be required. In this connection, by way of example, the carrier member for the anti-microbial agent and cleansing agent may be a film of the type that is absorbent or capable of carrying the anti-microbial agent and a cleansing agent. A foam is one form which can be applied directly to the surface of an animal or human and which is also capable of carrying the anti-microbial agent and cleansing agent. A sponge or brush can also be suitably modified to serve as an effective applicator to clean an animal or human skin surface.

Where cost is a primary consideration, it has been found that a low cost carrier member such as a bundle of paper strands may be employed and this will be particularly suitable for livestock or pets. It will be apparent to those skilled in the art that even a woven cloth or an unblended fiber cloth may be employed, although the non-woven fabric described above is preferred. Knitted, linen and other less costly fibers may also be employed in the construction of any of these fabric structures. A spun fabric can be particularly useful where the durability of the cloth is of primary concern.

The fabric may also be made with cellulose fibers, polyethylene, polypropylene, polyamide, and polyester fibers in both woven, non-woven and knitted constructions. It has been found that a carrier member made from fibers that are substantially collagen based can be particularly useful in circumstances where the skin surface requires a special treatment.

It will also be understood that the fabric need not be in substantially flat form but may be formed in a tubular structure such as a knitted tube similar to a stocking before closing of one end. A tubular knit article is particularly advantageous in terms of economy of manufacture when durability of the structure is of importance.

The carrier member may be made with a non-woven cloth as described above where the fibers are entangled by a fluid jet as well as mechanically. The use of a fluid jet may be in any form such as a liquid or gas. In these constructions, it may be desirable to bond the fibers at spaced points such as by use of an adhesive resin or by thermal bonding.

Figure 6:
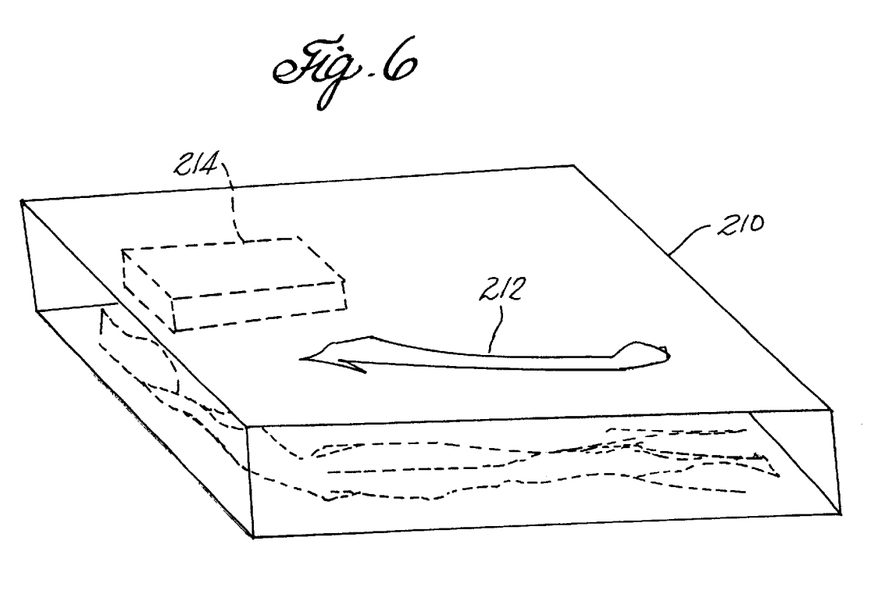
FIG. 6 is a schematic illustration of a further embodiment of the present invention.

To facilitate use of a cleansing article, as noted above, the use of a reclosable container such as that shown in FIG. 6 at 210 is preferred. Preferably the closure is by an interlocking snap grip formed by thickened portions of the lips defining the opening at 212. The container may also be reclosable by adhesive bonding or any similar method known to one skilled in the art. The material of the container may be polypropylene film and is preferably liquid impervious and substantially transparent to microwave radiation.

In many applications, it may be desirable to insert a heat retaining material in the container. Preferably this is done by providing an article such as a polyglycol or glycol containing sack which may be heated in a microwave oven and inserted into the container 210 as shown in the dotted line position at 214. This will enable a user to heat the container or simply the pouch containing the glycol and transport it to a site remote from the microwave for use. Alternatively, a heat retaining material such as foam or plastic, or any comparable substance capable of retaining heat known to those skilled in the art may be used.

The container itself is preferably also air impervious and for this object, polyester, polyamide, polypropylene, foil, nylon, or other comparable films are appropriate and can be successfully employed at relatively low cost. With such an arrangement, any water carrier will not evaporate that may be present in the solution carrying the anti-microbial agent and cleansing agent.

Preferably, to facilitate use, each of the articles, particularly those in cloth form, are folded and inserted into the container 210 so that a leading edge will be located adjacent the opening of the container for ease of access.

It will be apparent of course, that a single article may be inserted into such container for a limited application of the agents.

It will also be appreciated that various types of anti-microbial agents may be employed including but not limited to germicides, bactericides, virucides, sporicides, fungicides, and other toxic formulations particularly where the carrier member is going to be applied to non-human subjects. In this latter circumstance, a large number of vegetable as well as natural fibers may be employed and the choice of these types of fibers will largely depend on their availability at the time of manufacture.

Figures 5A, 5B:
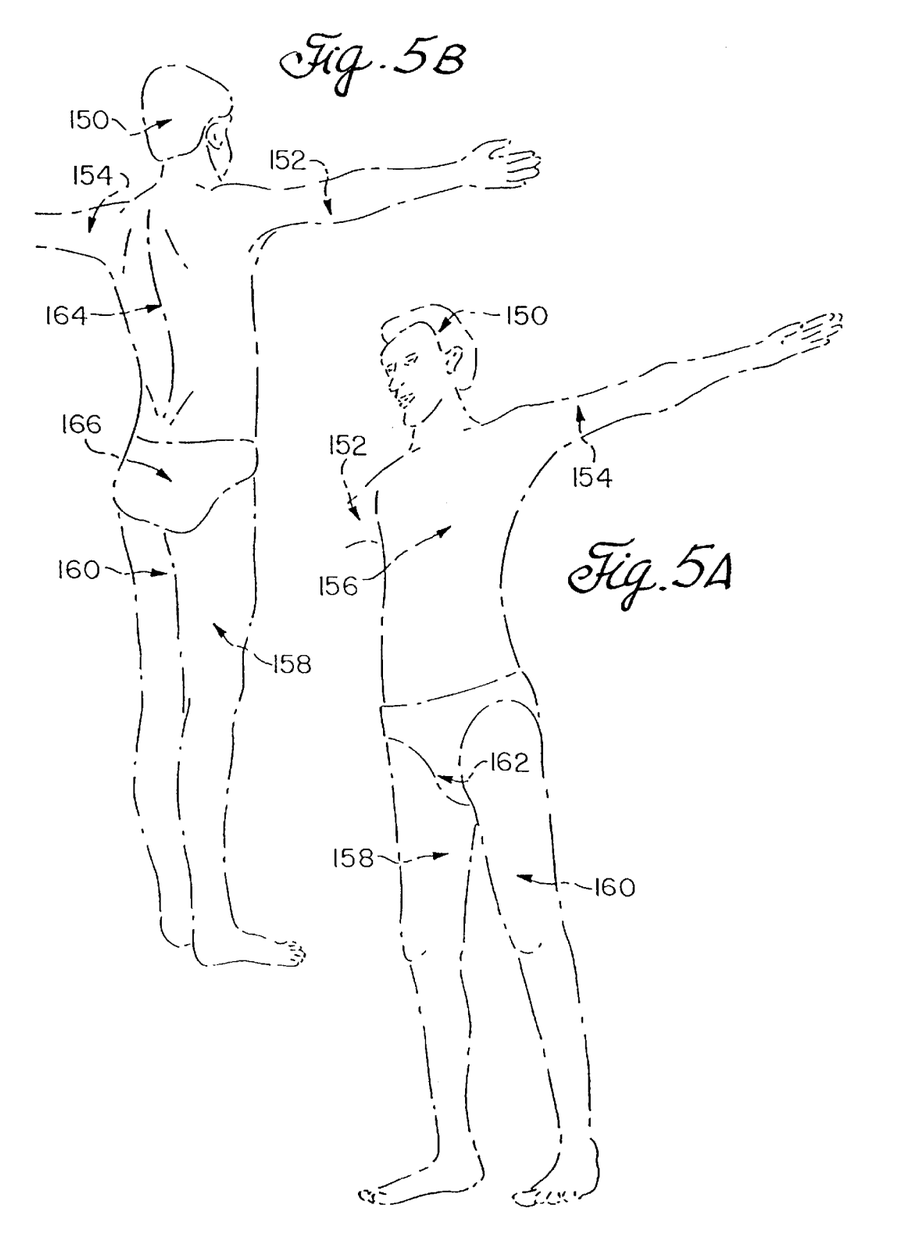
FIGS. 5a and 5b are an illustration of the zones of a human body for cleansing with a kit according to a preferred embodiment of the present invention.

The areas of the body are illustrated in FIGS. 5*a* and 5*b*. These areas include the head, neck and chest area 150, the right arm 152, the left arm 154, the right leg 158, the left leg 160, the perineum 162, the back 164 and the buttocks 166.

The following process is suggested to bathe the body. The first cloth 120 is used on the patient's face, neck and chest area 150. The first cloth 120 is then discarded and the second cloth 120 withdrawn from container 100. One, at a time, second and third cloths 120 are applied to the patient's right arm 152, including its axilla, and to his left arm 154, including the left axilla, respectively. The second and third cloths 120 are discarded as each one is used. The fourth cloth 120 is applied to the patient's right leg 158, discarded, and a fifth cloth 120 applied to his left leg 160, and it, too, is discarded. A sixth cloth 120 is removed and applied to the patient's perineal area 162. Finally, the seventh and eighth cloths 120 are applied to the patient's back 164 and buttocks 166, respectively, each being discarded after use.

Use of a kit in accordance with the preferred embodiments and method of the present invention is likely to avoid cross contamination and the spread of nosocomial infection, reduces the incidence of pressure ulcers and complies with the recommendations of the National Pressure Ulcer Advisory Panel and the AHCPR Guidelines. It provides a solution to the bathing needs of immuno-system suppressed individuals. It provides a portable, light-weight cleansing kit for individuals who have a stoma, such as ostomy, colostomy, and ileostomy, and who presently have a high risk of skin breakdown at the peri-stomal site, to cleanse without using soap, water and a wash cloth. It offers substantial cost savings over the former procedures. Furthermore, a kit accordingly to the present invention can be used for personal bathing, for example, for otherwise healthy individuals who are concerned with the condition of their skin or whose skin is at risk, such as the elderly, or when conventional bathing is not possible or practical, such as during emergencies, natural disasters, on board a sailboat or when camping.

It will be apparent to those skilled in the art that many changes and substitutions can be made to the preferred embodiment herein described without departing from the spirit and scope of the present invention as defined by the appended claims.

What is claimed is:

1. A method for washing two or more selected portions of a body comprising the steps of:
    (a) providing a factory-made sealed package containing a plurality of needle-punched non-woven cloths, each cloth carrying a cleanser;
    (b) removing a cloth from the package and using the removed cloth to wash only one selected portion of the body;
    (c) repeating step (b) until each selected portion of the body has been washed; and
    (d) disposing of each cloth after use.

2. The method of claim 1, wherein the number of selected body portions is at least four and the package contains at least four cloths.

3. The method of claim 1, wherein the number of selected body portions is at least eight and the package contains at least eight cloths.

4. The method according to claim 1 wherein the selected portions of the body include the head, the neck and chest area, the right arm, the left arm, the right leg, the left leg, the perineum, the back and the buttocks.

5. The method of claim 1, wherein the package contains at least ten cloths.

6. The method of claim 1, wherein each cloth comprises synthetic fibers.

7. The method of claim 1, wherein each cloth comprises natural fibers.

8. The method of claim 1, wherein each cloth comprises a blend of natural and synthetic fibers.

9. The method of claim 1, wherein the cleanser comprises a non-ionic surfactant.

10. The method of claim 1, wherein the cleanser has an acidic pH.

11. The method of claim 10, wherein the cleanser has a pH of about 5.5 to about 6.5.

12. The method of claim 1, wherein each cloth further carries an antimicrobial agent.

13. The method of claim 1, wherein each cloth further carries at least ingredient selected from the group consisting of vitamin E, humectants, emollients, and preservatives.

14. The method of claim 1, wherein, after each washing step, the portion of the body that is washed is not rinsed.

15. The method of claim 1, further comprising sterilizing the cloths in the sealed package.

16. The method of claim 1, wherein all of the cloths in the sealed package are used to wash selected portions of a single body.

\* \* \* \* \*